United States Patent [19]

Kassis et al.

[11] Patent Number: 4,534,483
[45] Date of Patent: Aug. 13, 1985

[54] CULTURE FLASK CLOSURE

[76] Inventors: Amin I. Kassis, 57 Stockdate Rd., Needham, Mass. 02192; Choukrie Akili-Mudarris, 533 Pleasant Wind Dr., Aberdeen, Md. 21001

[21] Appl. No.: 455,805

[22] Filed: Jan. 5, 1983

[51] Int. Cl.³ .................... B65D 55/16; C12M 1/24
[52] U.S. Cl. .................... 215/306; 206/509; 220/337; 222/543; 435/296
[58] Field of Search ............... 215/306, 252, 331, 258; 220/375, 339, 334, 335, 337, 265; 16/DIG. 13, 225, 227, 286; 222/498, 543, 517, 511; 435/296; 422/102, 104; 206/508, 509

[56] References Cited

U.S. PATENT DOCUMENTS

| 200,883 | 3/1878 | Weber . | |
|---|---|---|---|
| 1,924,242 | 8/1933 | Kaye | 215/306 |
| 2,704,100 | 3/1955 | Freeman . | |
| 2,737,312 | 3/1956 | Hamlon | 220/375 |
| 2,961,119 | 11/1960 | Leach . | |
| 2,977,973 | 4/1961 | Chakone | 215/306 X |
| 3,120,879 | 2/1964 | Warner | 222/543 |
| 3,199,707 | 8/1965 | Folkman . | |
| 3,243,068 | 3/1966 | Huston | 206/508 |
| 3,306,483 | 2/1967 | Bellafiore . | |
| 3,416,688 | 12/1968 | Fanning . | |
| 3,503,535 | 3/1970 | Sparks, Sr. | 220/326 |
| 3,518,164 | 6/1970 | Andelin et al. . | |
| 3,870,602 | 3/1975 | Froman et al. | 435/296 |
| 3,874,570 | 4/1975 | Katzman et al. | 222/543 |
| 3,933,271 | 1/1976 | McGure | 220/335 |
| 4,025,306 | 5/1977 | Studer . | |
| 4,062,652 | 12/1977 | Rolfo-Fontana . | |
| 4,109,814 | 8/1978 | Rausing . | |
| 4,334,028 | 6/1982 | Carver | 215/6 X |
| 4,377,247 | 3/1983 | Hazard et al. | 222/517 |
| 4,403,712 | 9/1983 | Wiesinger | 220/339 |

FOREIGN PATENT DOCUMENTS

| 2246277 | 9/1972 | Fed. Rep. of Germany | 220/375 |
|---|---|---|---|
| 964204 | 1/1950 | France | 222/543 |
| 1580404 | 7/1969 | France | 215/306 |

Primary Examiner—Allan N. Shoap
Assistant Examiner—Bryon Gehman

[57] ABSTRACT

A cell-culture flask which may be readily charged under sterile conditions, having a cap capable of covering its neck opening and an orientation strip attached to the flask at one end and to the cap at the opposite end; the orientation strip supports the cap in a first position in which the cap overlaps and covers the neck opening without sealing it; the strip is flexible to allow manual displacement of the cap away from that first position to a position in which the cap does not obstruct the introduction of a pipette into the opening; in the absence of displacing forces, the strip has a memory which returns the cap to the first position.

13 Claims, 7 Drawing Figures

U.S. Patent     Aug. 13, 1985     4,534,483
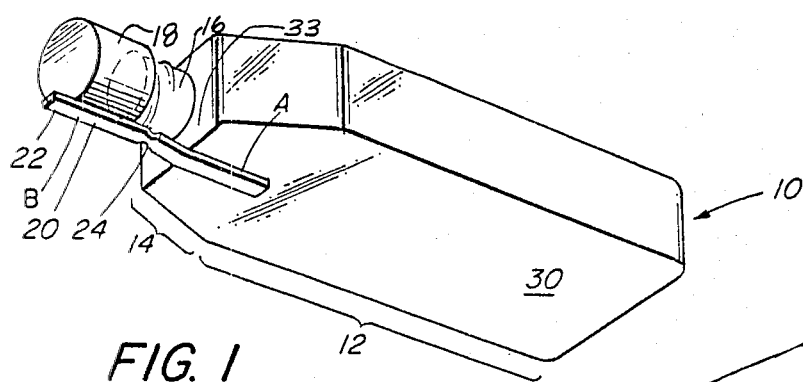
FIG. 1    FIG. 2
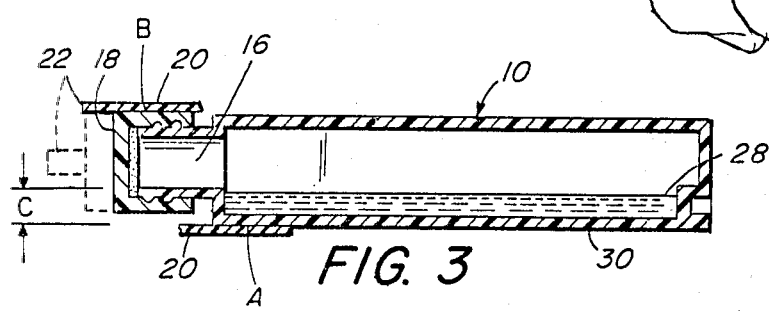
FIG. 3
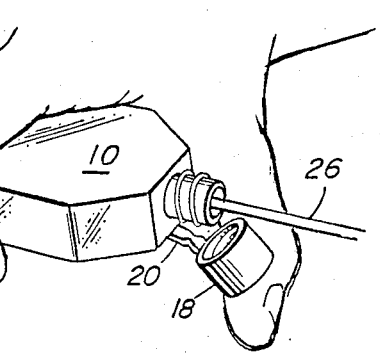
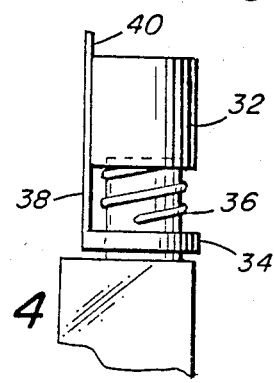
FIG. 4
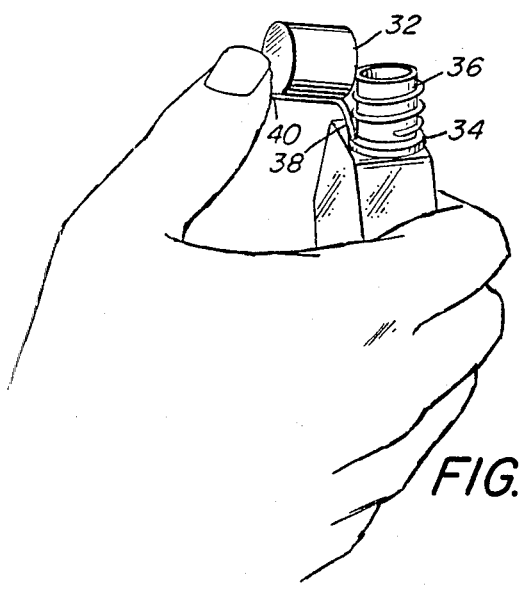
FIG. 5
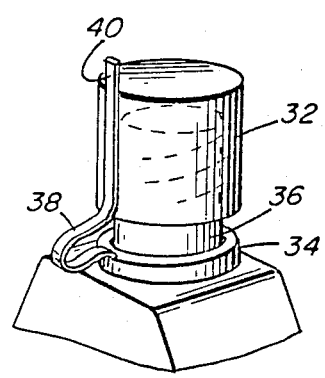
FIG. 6
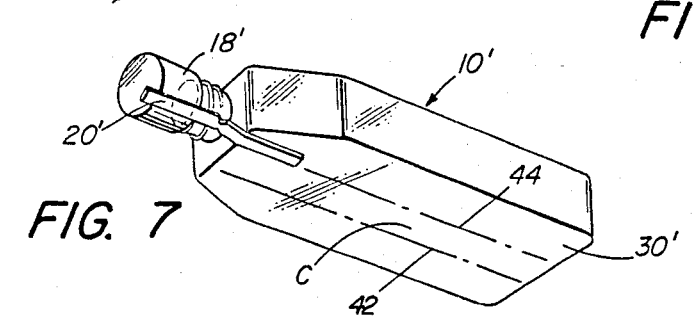
FIG. 7

CULTURE FLASK CLOSURE

BACKGROUND OF THE INVENTION

This invention relates to closure for flasks and other containers used in connection with incubating and culturing cells.

Cell-culture flasks must provide a sterile environment with adequate provision for exchange of gasses to sustain biological processes. Caps for such flasks must be capable of covering the flask opening without impeding the exchange of gasses (e.g., when the flask is in an incubator with a controlled atmosphere); in addition, it may be useful that the caps seal the falsk entirely, for example to protect its contents when the flask is outside of a controlled environment.

Maintaining sterile conditions within the flask while charging it with cells and a cell growth medium poses several problems. To charge the flask, the cap (usually a screw-on cap) is removed and the flask and cap are held. The flask is maintained in a slightly slanted orientation with respect to the horizontal, while a sterile pipette held in the other hand is used to charge the flask with cells and with culture medium. The cap is then replaced. During this procedure, the operator must hold the cap in a hand that is otherwise occupied (either with the flask or the pipette) and the operator must not touch the inner surfaces of the cap. For any given experiment, a large number of flasks may be required.

It is an object of this invention to provide a culture flask closure that allows quick and convenient charging of the flask while minimizing the chance of contamination and while providing the gas-exchange and flask-sealing advantages described above.

SUMMARY OF THE INVENTION

In one aspect, the invention features a cell-culture flask which may be readily charged under sterile conditions, having a cap capable of covering its neck opening and an orientation strip attached to the flask at one end and to the cap at the opposite end; the orientation strip supports the cap in a first position in which the cap overlaps and covers the neck opening without sealing it to passage of gasses and liquids; the strip is flexible to allow manual displacement of the cap away from that first position to a position in which the cap does not obstruct the introduction of a pipette into the opening; in the absence of displacing forces, the strip has a memory which returns the cap to the first position.

In preferred embodiments, the cap is capable of screwing onto the neck to seal it; the strip is a thermoplastic resinous material and has a weak point which is severed when the cap is screwed on; the strip extends along a wall section of the cap and extends perpendicular to, and above, a planar top section of the cap to terminate in an integral tab which facilitates manipulation of the cap away from the first position; the flask has the general configuration of a rectangular solid and the tab extends from the top of the cap at the point closest to the bottom face of that solid—i.e., the face on which the flask is designed to rest during culturing. The point of attachment of the strip to the flask body may be outside a central region on the bottom face, bounded by extensions of the neck which are parallel to the sides of that face; and the flask end has an indentation to accommodate the tab on the cap of a flask stacked in contact (cap-to-end) with it.

In another aspect, the invention features a reusable closure device for a container used in connection with cell culturing in which an orientation strip as described above is attached at one end to a screw cap for sealably closing the container neck, and at the other end to a collar which freely rotates about the container neck. Preferably, collar movement down the neck of the container in response to screwing the cap on is restricted at a point which causes bending of the orientation strip when the cap is tightly closed, so that unscrewing the cap allows the strip to straighten and provide a lifting force to aid removal of the cap from the container.

DESCRIPTION OF THE PREFERRED EMBODIMENTS

We turn now to a description of the preferred embodiments of the invention, first briefly describing the drawings thereof.

Drawings

FIG. 1 is a view of a flask according to the present invention, with the cap held in position overlapping the neck opening.

FIG. 2 is a view of the flask of FIG. 1, showing the process of charging the flask.

FIG. 3 is a cross-section of the charged flask, in position for incubation, with the orientation strip severed.

FIG. 4 is a view of an alternate embodiment of the invention including a reusable closure device supporting a screw cap in position over the container opening.

FIG. 5 is a view of the embodiment of FIG. 4 showing manual displacement of the cap after the cap has been unscrewed.

FIG. 6 is a view of the embodiment of FIG. 4 with the cap screwed tightly on.

FIG. 7 is a view of an alternate embodiment, similar to the embodiment of FIG. 1, having an offset orientation strip.

Structure

Turning first to FIG. 1, culture flask 10 has a body which includes a portion 12 having the general shape of a rectangular solid. The flask tapers in a neck region 14 to end in a cylindrical neck 16. Cap 18 has a planar top surface and a wall extending perpendicularly from the perimeter of that surface. Cap 18 has screw threads which mate with threads on cylindrical neck 16 to allow the cap to be screwed onto the neck.

Flask 10 is designed so that one face of the rectangular solid (face 30) is to be the bottom face during culturing. The distance C between face 30 and the point in cylindrical neck 16 closest to face 30 selected so that an adequate charge may be accommodated in the flask when it rests on a level surface on face 30, even though the neck opening is uncovered. Typically, neck 16 is placed further from face 30 than from the upper face (i.e., the face opposite face 30) so that mistakenly orienting the fully charged culture flask with face 30 up would allow the charge to spill from neck 16.

In FIG. 1, cap 18 is supported by orientation strip 20 in position so that the walls of the cap overlap cylindrical neck 16, thus covering the neck opening without sealing it, and allowing gas exchange between the inside of the container and its surrounding environment. Orientation 20 is attached to the body of flask 10 at point A and is attached to the wall of cap 18 at point B. Strip 20 extends along the wall of cap 18 and terminates above the top of the cap to form tab 22. Strip 20 narrows at 24 which is a weak point.

Strip 20 is made from a relatively stiff substance with a memory such that, when cap 18 is displaced and then released, the "memory" of the strip will return cap 18 to the position shown in FIG. 1, with the walls of cap 18 overlapping cylindrical portion of cylindrical neck 16. If the cap is not evenly seated on the threads of cylindrical neck 16 at this point, slight pressure on the top of cap 18 will achieve even seating of the cap so that the cap may readily be screwed on.

Strip 20 may be made, for example, from a resinous material that is thermoplastic such as polyethylene or polypropylene. It may be rectangular in cross-section, for example 3/32 inches by 1/64 inches. At the weak point, the strip is narrowed to about 1/64 inch in width. Other configurations are acceptable, so long as the strip is easily manipulated to move the cap away from the neck opening, and so long as the strip has sufficient strength and memory to return the cap to the orientation described above (FIG. 1) and to support it in that orientation.

Operation

An empty flask such as that shown in FIG. 1 is removed (usually in a controlled laboratory atmosphere) from a sterile wrapping used for packaging and shipment. As shown in FIG. 1, cap 18 is supported in position with the cap walls overlapping cylindrical neck 16.

To charge the flask, the operator holds the flask with face 30 down, and uses his thumb to displace cap 18 from cylindrical neck 16 by exerting a slight sideward displacement force on tab 22 with his thumb. Pipette 26, held in the operator's other hand is introduced into the neck opening and the charge (cells or cell nutrients, introduced in separate steps) is expelled from the pipette. During this procedure, the operator must exercise care not to touch the inner surfaces of the cap, which would contaminate it. The operator also must not allow the cell charge to wash upper surface of the flask, because the experimental measurement at issue involves a cell count, and cells stranded on upper walls will die, thus artificially lowering the cell count. The placement of tab 22, as an extension from the point on the perimeter of cap 18 that is closest to face 30, serves as a key to alert the operator that face 30 is the bottom face, thus avoiding mistaken orientation of the flask, and resulting contact of the charge with upper flask walls.

Once the flask is charged, the operator releases tab 22 and the memory of strip 20 causes it to return to the position shown in FIG. 1. If necessary, a very slight adjustment using pressure on the top of cap 18 will seat the cap on the threads of cylindrical neck 16.

Once the cap has been seated evenly on the cylindrical threads, it may be screwed tight (if desired), thus breaking strip 20 at weak point 24, and the flask may be transported through a non-sterile atmosphere to the incubator. In the incubator, the cap is loosened to allow gas transfer with the surrounding atmosphere, as shown in FIG. 3.

FIGS. 4, 5 and 6, show an alternate reusable embodiment, suitable for a culture flask or for a container to store cells or cell culture medium. Cap 32 is attached by strip 38 to collar 34 which is free to turn loosely around cylindrical neck 36. Tab 40 extends from the top of cap 32.

In operation, strip 38, when fully extended, maintains cap 32 loosely over the cylindrical neck so that the sides of the cap overlap the neck. The operator may use his thumb against tab 40 to displace the cap from this configuration and insert a pipette (e.g., to charge the flask if the container is a flask, or to remove cells or cell culture medium if the container is a storage bottle).

When tab 40 is released, strip 38 returns the cap to the orientation of FIG. 4 in a manner similar to that described above for the embodiment of FIG. 1–3. The cap may then be seated on the threads and screwed on. In so doing, collar 34 turns freely around cylindrical portion 36, and both the collar and cap are lowered down the neck until the collar is stopped against the flask body. At that point, additional tightening of cap 32 compresses strip 38 as shown in FIG. 6.

Unscrewing the cap releases the spring force stored in strip 38 and aids in removal of the cap from the neck.

OTHER EMBODIMENTS

Other embodiments are within the following claims. For example, the orientation strip may be made of other materials, and the weak point of the strip shown in the embodiment of FIGS. 1–3, may be along the strip, or at the point of attachment of the strip to the flask or to the cap. The orientation strip may be attached to any convenient point on the flask, and need not be attached to face 30. For example, the strip may be attached to surface 33 in FIG. 1. The strip may also be attached to the face opposite bottom face 30, and, so long as this practice is consistent and the operator knows of it, such an attachment orientation provides a "key" to warn against inadvertant misorientation of the flask.

As shown in FIG. 7 point of attachment of the orientation strip and the flask body (point A) may be off of the longitudinal center line of face 30'—i.e., outside of the central region C bounded by extensions 42 and 44 of the neck which are parallel to the sides of face 30'—so that the operator may hold several flasks in one hand at the same time ( with the flasks back-to-front) and the neck of one flask will not interfere with the displacement of the cap of the flask next to it.

It is not necessary that the cap be capable of completely sealing the flask opening against the passage of gasses of liquids, so long as it covers the opening to prevent entry to dust or debris; thus the cap need not have a screw seal or a snap seal.

Also the flask body may contain an indentation on the flask face opposite the neck so that, when the flasks are placed top-to-end (e.g., in shipment) the identation will accommodate tab 22 from the flask next to it, thereby avoiding damage to the tab.

What is claimed is:

1. In a cell-culture flask comprising a flask body with a neck comprising a wall that defines an opening to said body and a generally tubular cap including means for covering said neck opening, that improvement comprising:

(a) an orientation strip attached at one end to said flask and at the opposite end to said cap, said strip along a portion of its extent being securely fastened to the tubular said wall of said cap along a substantially straight line, said strip having sufficient strength to support said cap in a protective position in which the cap overlaps and covers said neck opening and the lower portion of said cap is immediately adjacent the upper portion of said neck, said strip comprising an elongated connecting section between said cap and said flask, said connecting section being substantially in a straight line with said portion of said strip securely fastened to said cap when said cap is in said protective position, said strip having sufficient flexibility to allow manual displacement of said cap readily from said protective position to a second position in which said cap does not obstruct the introduction of a pipette into said opening, said strip having a memory to return said cap to said protective position from all operative positions other than said protective position in the absence of any force external to said cap tending to move said cap away from said protective position; and (b) a tab extending above the top of said cap in a direction generally parallel to the axis of said cap, whereby said flask may be readily charged while maintaining sterile conditions, by manually displacing said cap from said protective position to said second position facilitated by said tab, inserting a pipette into said opening, discharging the contents of said pipette into said flask, removing said pipette from said flask, and allowing said cap to return to said protective position.

2. The flask of claim 1 further characterized in that said cap includes means for sealably closing said neck opening comprising screw threads on said cap and mating screw threads on said neck.

3. The flask of claim 2 further characterized in that said orientation strip comprises a weak point designed to sever upon manual twisting of said cap relative to said flask body to engage said mating screw threads.

4. The flask of claim 1 further characterized in that a tab extends above the top of said cap, whereby manipulation of said cap from said protective position to said second position is facilitated.

5. The flask of claim 4 further characterized in that said cap comprises a planar top section and a wall section extending downwardly from the perimeter of said top section, said tab extending beyond said perimeter generally above and perimeter to said top section.

6. The flask claim 4 further characterized in that said tab is integral with said orientation strip.

7. The flask of claim 4 further characterized in that said flask body, excluding said neck, has the general configuration of a rectangular solid, one face of which serves as the bottom face during the cell culture process, the point in said neck opening closest to said bottom face is sufficiently above said bottom face to allow said flask to accommodate the desired charge with said neck opening uncovered, and said tab extends from the top of said cap at the point closest to said bottom face, whereby an operator charging said flask is alerted to the proper orientation of said flask when handling said flask, and thereby may avoid contacting upper surfaces of said flask with cells.

8. The flask of claim 7 further characterized in that said orientation strip is attached to said flask body at a point on a face of said flask, said attachment point lying outside a central region on said face bounded to extensions of said neck parallel to the sides of said flask face, whereby said flask cap may be manipulated to said second position without interfering with the neck of a second flask stacked in contact with said face of said first flask.

9. The flask of claim 7 further characterized in that the end of said flask opposite said neck opening contains an indentation sized to receive a tab from a second flask stacked top-to-end with said first flask.

10. The flask of claim 1 further characterized in that said orientation strip is resinous material.

11. The flask of claim 1 further characterized in that said orientation strip is thermoplastic material.

12. A reusable closure device for a container with a threaded neck comprising a wall defining an opening to the interior thereof, said container being used in connection with cell culturing, said device comprising a generally cylindrical screw-up for threadably sealably closing said neck opening, a collar which encircles and freely turns about said neck opening, and an orientation strip attached at one end to said cap and at the opposite end to said collar said strip along a portion of its extent being securely fastened to the cylindrical side wall of said cap along a substantially straight line said strip having sufficient strength to support said container cap in a first position in which the cap overlaps and covers said neck opening without threadably, sealably closing said opening and the lower portion of said cap is immediately adjacent the said srip having sufficient flexibility to allow manual displacement of said cap from said first position to a second position in which said cap does not obstruct the introduction of a pipette into said opening, said strip comprising an elongated connecting section between said cap and said flask, said connecting section being substantially in a straight line with said portion of said strip securely fastened to said cap when said cap is in said first position, said strip having a memory to return said cap to said first position from all operative positions other than said first position in the absence of any force external to said cap tending to move said cap away from said first position, said container further comprising a tab extending above the top of said cap in a direction generally parallel to the axis of said cap, to facilitate displacement of said cap from said first position, whereby access to the interior of said container is achieved while maintaining sterile conditions.

13. The device of claim 12 further characterized in that said flask comprises a stop against collar movement down said neck is response to screwing action to close said neck opening, whereby fully closing said opening with said cap causes said strip to bend and provide a spring force when said cap is loosened, to facilitate removal of said cap from said container.

* * * * *

UNITED STATES PATENT AND TRADEMARK OFFICE
CERTIFICATE OF CORRECTION

PATENT NO. : 4,534,483
DATED : August 13, 1985
INVENTOR(S) : Amin I. Kassis et al.

It is certified that error appears in the above-identified patent and that said Letters Patent are hereby corrected as shown below:

Under References Cited, "Chakone" should be --Chakine--; and "McGure" should be --McGhie--;

Column 3, line 37, "surface" should be --surfaces--;

Column 5, line 37, "perimeter" should be --perpendicular--;

Column 6, line 30, add after "adjacent the", --upper portion of said neck--;

Column 6, line 31, "strip" is misspelled.

Signed and Sealed this

Twelfth Day of November 1985

[SEAL]

Attest:

DONALD J. QUIGG

Attesting Officer

Commissioner of Patents and Trademarks